(12) United States Patent
Barnes et al.

(10) Patent No.: US 7,057,026 B2
(45) Date of Patent: Jun. 6, 2006

(54) LABELLED NUCLEOTIDES

(75) Inventors: Colin Barnes, Nr. Saffron Walden (GB); Shankar Balasubramanian, Nr. Saffron Walden (GB); Xiaohai Liu, Nr. Saffron Walden (GB); Harold Swerdlow, Nr. Saffron Walden (GB); John Milton, Nr. Saffron Walden (GB)

(73) Assignee: Solexa Limited, Nr. Saffron Walden (GB)

( * ) Notice: Subject to any disclaimer, the term of this patent is extended or adjusted under 35 U.S.C. 154(b) by 336 days.

(21) Appl. No.: 10/227,131

(22) Filed: Aug. 23, 2002

(65) Prior Publication Data

US 2003/0104437 A1 Jun. 5, 2003

(51) Int. Cl.
*C07H 21/00* (2006.01)
*C07H 21/02* (2006.01)
*C07H 21/04* (2006.01)
*C12Q 1/68* (2006.01)

(52) U.S. Cl. .................. 536/23.1; 435/6; 435/91.1; 435/287.2; 536/25.3; 536/26.6

(58) Field of Classification Search ............ 435/6, 435/91.1, 287.2; 536/23.1, 25.3, 26.6
See application file for complete search history.

(56) References Cited

U.S. PATENT DOCUMENTS

| 4,772,691 | A | 9/1988 | Herman |
|---|---|---|---|
| 5,302,509 | A | 4/1994 | Cheeseman |
| 5,436,143 | A | 7/1995 | Hyman |
| 5,516,664 | A | 5/1996 | Hyman |
| 5,547,839 | A | 8/1996 | Dower et al. |
| 5,602,000 | A | 2/1997 | Hyman |
| 5,763,594 | A | 6/1998 | Hiatt et al. |
| 5,872,244 | A | 2/1999 | Hiatt et al. |
| 6,008,379 | A | 12/1999 | Benson et al. |
| 6,087,095 | A | 7/2000 | Rosenthal et al. |
| 6,214,987 | B1 | 4/2001 | Hiatt et al. |
| 6,255,475 | B1 | 7/2001 | Kwiatkowski |
| 6,664,079 | B1 * | 12/2003 | Ju et al. ............... 435/91.1 |

FOREIGN PATENT DOCUMENTS

| WO | WO 94/14972 | 7/1994 |
|---|---|---|
| WO | WO 96/07669 | 3/1996 |
| WO | WO 99/05315 | 2/1999 |
| WO | WO 99/57321 | 11/1999 |
| WO | WO 00/02895 | 1/2000 |
| WO | WO 00/15844 | 3/2000 |
| WO | WO 00/53812 | 9/2000 |
| WO | WO 01/23610 | 4/2001 |
| WO | WO 01/57249 | 8/2001 |
| WO | WO 02/29003 | 4/2002 |

OTHER PUBLICATIONS

Stragene Catalog 1988 p. 39.*
J. Brunckova et al., Tetrahedron Letters, 1994, vol. 35, pp. 6619-6622.
S. Nishino et al., Heteroatom Chemistry, 1991, vol. 2, pp. 187-196.

(Continued)

*Primary Examiner*—Jezia Riley
(74) *Attorney, Agent, or Firm*—Klauber & Jackson LLC

(57) ABSTRACT

Nucleosides and nucleotides are disclosed that are linked to detectable labels via a cleavable linker group.

8 Claims, 6 Drawing Sheets

OTHER PUBLICATIONS

M. Krečmerová, Coll. Czech. Chem. Commun., 1990 vol. 55, pp. 2521-2536.

P. J. L. M. Quaedflieg et al., Tetrahedron Letters, 1992 vol. 33, pp. 3081-3084.

J. I. Yamashita et al., Chem Pharm. Bull., 1987, vol. 35, pp. 2373-2381.

S.G. Zavgorodny et al., Nucleosides, Nucleotides and Nucleic Acids, 19(10-12), 1977-1991 (2000).

* cited by examiner

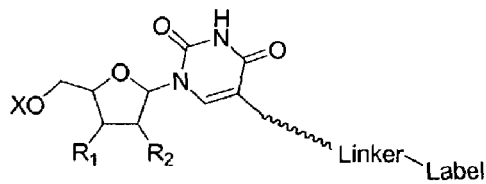

Uridine C5-linker

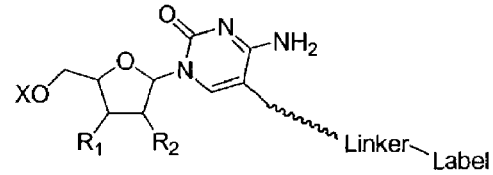

Cytidine C5-linker

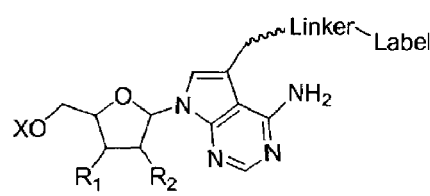

N7 Deazaadenosine C7-linker

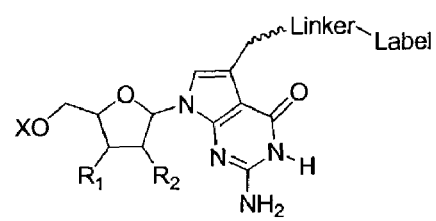

N7 Deazaguanosine C7-linker

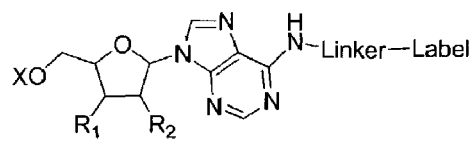

Adenosine N6-linker

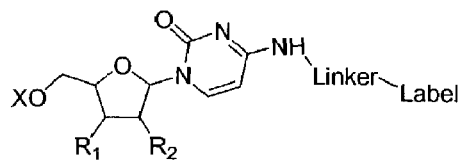

Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

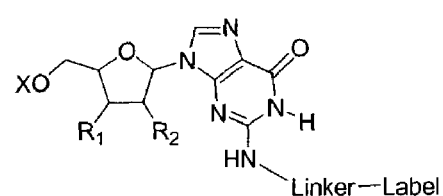

Guanosine N2-linker

Fig. 1

Label ~~~Cleavable linker~~~~Base

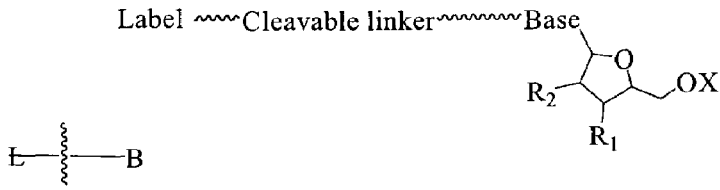

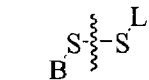

Cleavable linkers may include:

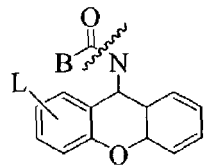

where $R_1$ and $R_2$, which may be the same or different, are each selected from H, OH, or any group which can be transformed into an OH, including a carbonyl $R_1$ and $R_2$ groups may include

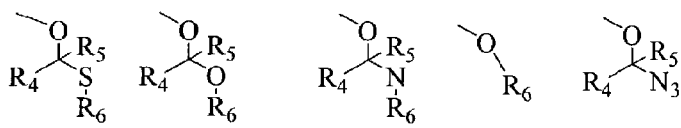

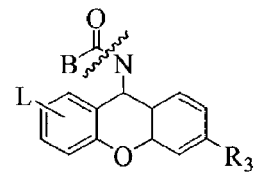

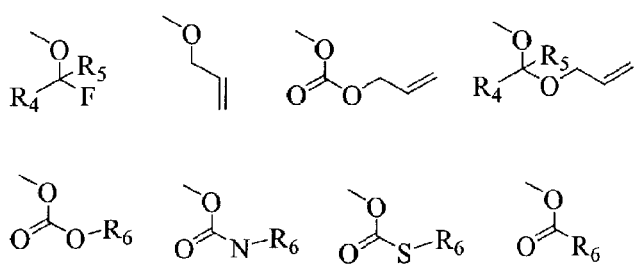

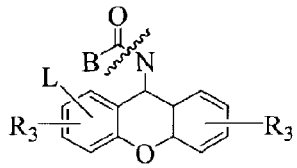

R3 represents one or more substituents independently selected from alkyl, alkoxy, amino or halogen

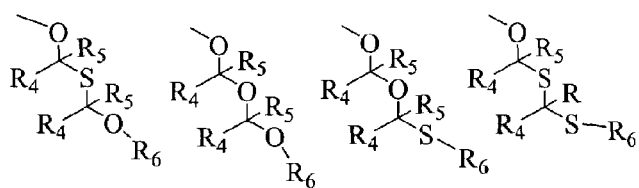

Alternatively, cleavable linkers may be constructed from any labile functionality used on the 3'-block

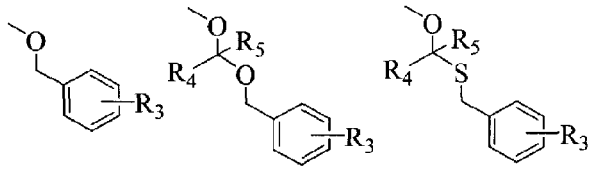

where $R_4$ is H or alkyl, $R_5$ is H or alkyl and $R_6$ is alkyl, cycloalkyl, alkenyl, cycloalkenyl or benzyl and X is H, phosphate, diphosphate or triphosphate

Fig. 3

LABELLED NUCLEOTIDES

RELATED APPLICATION

This application claims benefit of United Kingdom Application No. GB0129012.1, filed Dec. 4, 2001. The entire teachings of the above application are incorporated herein by reference.

FIELD OF THE INVENTION

This invention relates to labelled nucleotides. In particular, this invention discloses nucleotides having a removable label and their use in polynucleotide sequencing methods.

BACKGROUND

Advances in the study of molecules have been led, in part, by improvement in technologies used to characterise the molecules or their biological reactions. In particular, the study of the nucleic acids DNA and RNA has benefited from developing technologies used for sequence analysis and the study of hybridisation events.

An example of the technologies that have improved the study of nucleic acids, is the development of fabricated arrays of immobilised nucleic acids. These arrays consist typically of a high-density matrix of polynucleotides immobilised onto a solid support material. See, e.g., Fodor et al., *Trends Biotech.* 12:19–26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci. USA* 92:6379–6383, 1995).

A further development in array technology is the attachment of the polynucleotides to the solid support material to form single molecule arrays. Arrays of this type are disclosed in International Patent App. WO 00/06770. The advantage of these arrays is that reactions can be monitored at the single molecule level and information on large numbers of single molecules can be collated from a single reaction.

For DNA arrays to be useful, the sequences of the molecules must be determined. U.S. Pat. No. 5,302,509 discloses a method to sequence polynucleotides immobilised on a solid support. The method relies on the incorporation of 3'-blocked bases A, G, C and T having a different fluorescent label to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

Welch et al. (*Chem. Eur. J.* 5(3):951–960, 1999) describes the synthesis of nucleotide triphosphates modified with a 3'-O-blocking group that is photolabile and fluorescent. The modified nucleotides are intended for use in DNA sequencing experiments. However, these nucleotides proved to be difficult to incorporate onto an existing polynucleotide, due to an inability to fit into the polymerase enzyme active site.

Zhu et al. (*Cytometry* 28:206–211, 1997) also discloses the use of fluorescent labels attached to a nucleotide via the base group. The labelled nucleotides are intended for use in fluorescence in situ hybridisation (FISH) experiments, where a series of incorporated labelled nucleotides is required to produce a fluorescent "bar code".

SUMMARY OF THE INVENTION

In the present invention, a nucleoside or nucleotide molecule is linked to a detectable label via a cleavable linker group attached to the base, rendering the molecule useful in techniques using Labelled nucleosides or nucleotides, e.g., sequencing reactions, polynucleotide synthesis, nucleic acid amplification, nucleic acid hybridization assays, single nucleotide polymorphism studies, and other techniques using enzymes such as polymerases, reverse transcriptases, terminal transferases, or other DNA modifying enzymes. The invention is especially useful in techniques that use Labelled dNTPs, such as nick translation, random primer labeling, end-labeling (e.g., with terminal deoxynucleotidyltransferase), reverse transcription, or nucleic acid amplification. The molecules of the present invention are in contrast to the prior art, where the label is attached to the ribose or deoxyribose sugar, or where the label is attached via a non-cleavable linker.

According to a first aspect of the invention, a nucleotide or nucleoside molecule, or an analog thereof, has a base that is linked to a detectable label via a cleavable linker.

The invention features a nucleotide or nucleoside molecule, having a base that is linked to a detectable label via a cleavable linker. The base can be a purine, or a pyrimidine. The base can be a deazapurine. The molecule can have a ribose or deoxyribose sugar moiety. The ribose or deoxyribose sugar can include a protecting group attached via the 2' or 3' oxygen atom. The protecting group can be removed to expose a 3'-OH. The molecule can be a deoxyribonucleotide triphosphate. The detectable label can be a fluorophore. The linker can be an acid labile linker, a photolabile linker, or can contain a disulphide linkage.

The invention also features a method of labeling a nucleic acid molecule, where the method includes incorporating into the nucleic acid molecule a nucleotide or nucleoside molecule, where the nucleotide or nucleoside molecule has a base that is linked to a detectable label via a cleavable linker. The incorporating step can be accomplished via a terminal transferase, a polymerase or a reverse transcriptase. The base can be a purine, or a pyrimidine. The base can be a deazapurine. The nucleotide or nucleoside molecule can have a ribose or deoxyribose sugar moiety. The ribose or deoxyribose sugar can include a protecting group attached via the 2' or 3' oxygen atom. The protecting group can be removed to expose a 3'-OH group. The molecule can be a deoxyribonucleotide triphosphate. The detectable label can be a fluorophore. The linker can be an acid labile linker, a photolabile linker, or can contain a disulphide linkage. The detectable label and/or the cleavable linker can be of a size sufficient to prevent the incorporation of a second nucleotide or nucleoside into the nucleic acid molecule.

In another aspect, the invention features a method for determining the sequence of a target single-stranded polynucleotide, where the method includes monitoring the sequential incorporation of complementary nucleotides, where the nucleotides each have a base that is linked to a detectable label via a cleavable linker, and where the identity of each nucleotide incorporated is determined by detection of the label linked to the base, and subsequent removal of the label.

The invention also features a method for determining the sequence of a target single-stranded polynucleotide, where the method includes: (a) providing nucleotides, where the nucleotides have a base that is linked to a detectable label via a cleavable linker, and where the detectable label linked to each type of nucleotide can be distinguished upon detection from the detectable label used for other types of nucleotides; (b) incorporating a nucleotide into the complement of the target single stranded polynucleotide; (c) detecting the label of the nucleotide of (b), thereby determining the type of nucleotide incorporated; (d) removing the label of the nucleotide of (b); and (e) optionally repeating steps (b)–(d) one or more times; thereby determining the sequence of a target single-stranded polynucleotide.

In the methods described herein, each of the nucleotides can be brought into contact with thew target sequentially, with removal of non-incorporated nucleotides prior to addition of the next nucleotide, where detection and removal of the label is carried out either after addition of each nucleotide, or after addition of all four nucleotides.

In the methods, all of the nucleotides can be brought into contact with the target simultaneously, i.e., a composition comprising all of the different nucleotides is brought into contact with the target, and non-incorporated nucleotides are removed prior to detection and subsequent to removal of the label(s).

The methods can comprise a first step and a second step, where in the first step, a first composition comprising two of the four nucleotides is brought into contact with the target, and non-incorporated nucleotides are removed prior to detection and subsequent to removal of the label, and where in the second step, a second composition comprising the two nucleotides not included in the first composition is brought into contact with the target, and non-incorporated nucleotides are removed prior to detection and subsequent to removal of the label, and where the first steps and the second step can be optionally repeated one or more times.

The methods described herein can also comprise a first step and a second step, where in the first step, a composition comprising one of the four nucleotides is brought into contact with the target, and non-incorporated nucleotides are removed prior to detection and subsequent to removal of the label, and where in the second step, a second composition comprising the three nucleotides not included in the first composition is brought into contact with the target, and non-incorporated nucleotides are removed prior to detection and subsequent to removal of the label, and where the first steps and the second step can be optionally repeated one or more times.

The methods described herein can also comprise a first step and a second step, where in the first step, a first composition comprising three of the four nucleotides is brought into contact with the target, and non-incorporated nucleotides are removed prior to detection and subsequent to removal of the label, and where in the second step, a composition comprising the nucleotide not included in the first composition is brought into contact with the target, and non-incorporated nucleotides are removed prior to detection and subsequent to removal of the label, and where the first steps and the second step can be optionally repeated one or more times.

In a further aspect, the invention features a kit, where the kit includes: (a) individual the nucleotides, where each nucleotide has a base that is linked to a detectable label via a cleavable linker, and where the detectable label linked to each nucleotide can be distinguished upon detection from the detectable label used for other three nucleotides; and (b) packaging materials therefor. The kit can further include an enzyme and buffers appropriate for the action of the enzyme.

The nucleotides/nucleosides are suitable for use in many different DNA-based methodologies, including DNA synthesis and DNA sequencing protocols.

According to another aspect of the invention, a method for determining the sequence of a target polynucleotide comprises monitoring the sequential incorporation of complementary nucleotides, wherein the nucleotides comprise a detectable label linked to the base portion of the nucleotide via a cleavable linker, incorporation is detected by monitoring the label, and the label is removed to permit further nucleotide incorporation to occur.

DECRIPTION OF THE DRAWINGS

FIG. 1 shows examplary nucleotide structures useful in the invention. For each structure, X can be H, phosphate, diphosphate or triphosphate. $R_1$ and $R_2$ can be the same or different, and can be selected from H, OH, or any group which can be transformed into an OH, including, but not limited to, a carbonyl. Some suitable functional groups for $R_1$ and $R_2$ include the structures shown in FIG. 3.

FIG. 2 shows structures of linkers useful in the invention, including (1) disulfide linkers and acid labile linkers, (2) dialkoxybenzyl linkers, (3) Sieber linkers, (4) indole linkers and (5) t-butyl Sieber linkers.

FIG. 3 shows some functional molecules useful in the invention, including some cleavable linkers and some suitable hydroxyl protecting groups. In these structures, $R_1$ and $R_2$ may be the same of different, and can be H, OH, or any group which can be transformed into an OH group, including a carbonyl. $R_3$ represents one or more substituents independently selected from alkyl, alkoxyl, amino or halogen groups. Alternatively, cleavable linkers may be constructed from any labile functionality used on the 3'-block. $R_4$ and $R_5$ can be H or alkyl, and $R_6$ can be alkyl, cycloalkyl, alkenyl, cycloalkenyl or benzyl. X can be H, phosphate, diphosphate or triphosphate.

DETAILED DESCRIPTION

Figure 2:
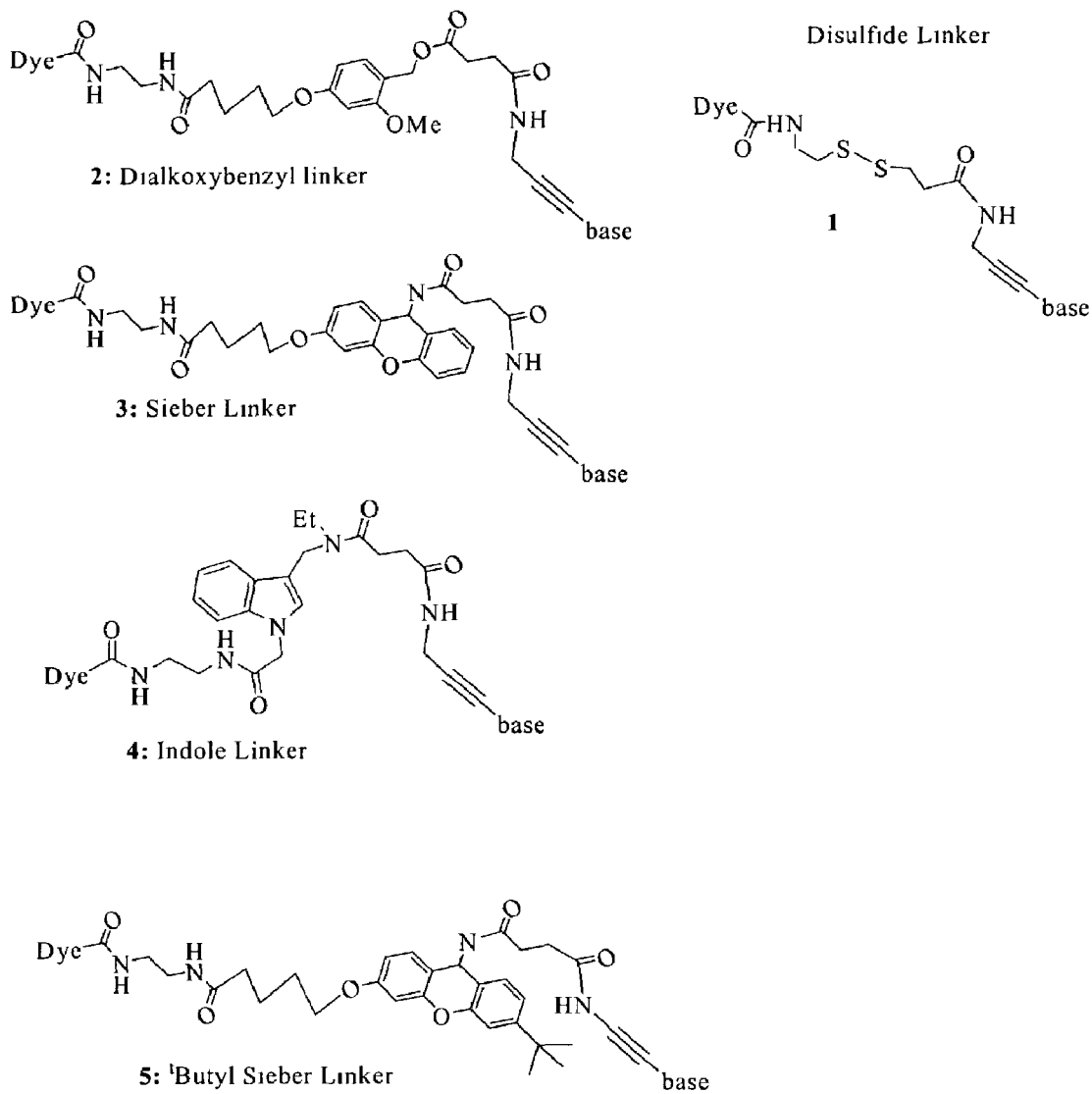

The present invention relates to nucleotides and nucleosides that are modified by attachment of a label via a cleavable linker, thereby rendering the molecule useful in techniques where the labelled molecule is to interact with an enzyme, such as sequencing reactions, polynucleotide synthesis, nucleic acid amplification, nucleic acid hybridization assays, single nucleotide polymorphism studies, techniques using enzymes such as polymerase, reverse transcriptase, terminal transferase, techniques that use Labelled dNTPs (e.g., nick translation, random primer labeling, end-labeling (e.g., with terminal deoxynucleotidyltransferase), reverse transcription, or nucleic acid amplification).

As is known in the art, a "nucleotide" consists of a nitrogenous base, a sugar, and one or more phosphate groups. In RNA, the sugar is a ribose, and in DNA is a deoxyribose, i.e., a sugar lacking a hydroxyl group that is present in ribose. The nitrogenous base is a derivative of purine or pyrimidine. The purines are adenosine (A) and guanidine (G), and the pyrimidines are cytidine (C) and thymidine (T) (or in the context of RNA, uracil (U)). The C-1 atom of deoxyribose is bonded to N-1 of a pyrimidine or N-9 of a purine. A nucleotide is also a phosphate ester of a nucleoside, with esterification occurring on the hydroxyl group attached to C-5 of the sugar. Nucleotides are usually mono, di- or triphosphates.

A "nucleoside" is structurally similar to a nucleotide, but are missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogs are available which do not alter the capability of the nucleotide or nucleoside to undergo Watson-Crick base pairing. "Derivative" or "analog" means a compound or molecule whose core structure is the same as, or closely resembles that of, a parent compound, but which has a chemical or physical modification, such as a different or additional side groups, which allows the derivative nucleotide or nucleoside to be linked to another molecule. For example, the base can be a deazapurine. The derivatives should be capable of undergoing Watson-Crick pairing. "Deivative" and "analog" also mean a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543–584, 1990. Nucleotide analogs can also comprise modified phosphodiester linkages, including phosphorothioate, phosphorodithioate, alkylphosphonate, phosphoranilidate and phosphoramidate linkages. The analogs should be capable of undergoing Watson-Crick base pairing. "Derivative" and "analog", as used herein, may be used interchangeably, and are encompassed by the terms "nucleotide" and "nucleoside" as defined herein.

The present invention can make use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3): 951–960, 1999) discloses dansyl-functionalised fluorescent moieties that can be used in the present invention. Zhu et al. (*Cytometry* 28:206–211, 1997) describes the use of the fluorescent labels Cy3 and Cy5, which can also be used in the present invention. Labels suitable for use are also disclosed in Prober et al. (*Science* 238:336–341, 1987); Connell et al. (*BioTechniques* 5(4):342–384, 1987), Ansorge et al. (*Nucl. Acids Res.* 15(11):4593–4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the invention. For example, bi-fluorophore FRET cassettes (*Tet. Letts.* 46:8867–8871, 2000) are well known in the art and can be utilised in the present invention. Multi-fluor dendrimeric systems (*J. Amer. Chem. Soc.* 123:8101–8108, 2001) can also be used.

Although fluorescent labels are preferred, other forms of detectable labels will be apparent as useful to those of ordinary skill. For example, microparticles, including quantum dots (Empodocles, et al., *Nature* 399:126–130, 1999), gold nanoparticles (Reichert et al., *Anal. Chem.* 72:6025–6029, 2000), microbeads (Lacoste et al., *Proc. Natl. Acad. Sci USA* 97(17):9461–9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

The label (or label and linker construct) can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

The invention will be further described with reference to nucleotides. However, unless indicated otherwise, the reference to nucleotides is also intended to be applicable to nucleosides. The invention will also be further described with reference to DNA, although the description will also be applicable to RNA, PNA, and other nucleic acids, unless otherwise indicated.

The modified nucleotides of the invention use a cleavable linker to attach the label to the nucleotide. The use of a cleavable linker ensures that the label can, if required, be removed after detection, avoiding any interfering signal with any labelled nucleotide incorporated subsequently.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidising agents, light, temperature, enzymes etc. Suitable linkers can be adapted from standard chemical blocking groups, as disclosed in Greene & Wuts, *Protective Groups in Organic Synthesis*, John Wiley & Sons. Further suitable cleavable linkers used in solid-phase synthesis are disclosed in Guillier et al. (*Chem. Rev.* 100:2092–2157, 2000).

The use of the term "cleavable linker" is not meant to imply that the whole linker is required to be removed from the nucleotide base. The cleavage site can be located at a position on the linker that ensures that part of the linker remains attached to the nucleotide base after cleavage.

The linker can be attached at any position on the nucleotide base provided that Watson-Crick base pairing can still be carried out. In the context of purine bases, it is preferred if the linker is attached via the 7 position of the purine or the preferred deazapurine analogue, via an 8-modified purine, via an N-6 modified adenosine or an N-2 modified guanine. For pyrimidines, attachment is preferably via the 5 position on cytidine, thymidine or uracil and the N-4 position on cytosine. Suitable nucleotide structures are shown in FIG. 1. For each structure in FIG. 1, X can be H, phosphate, diphosphate or triphosphate. $R_1$ and $R_2$ can be the same or different, and can be selected from H, OH, or any group which can be transformed into an OH, including, but not limited to, a carbonyl. Some suitable functional groups for $R_1$ and $R_2$ include the structures shown in FIG. 3.

Suitable linkers are shown in FIG. 2 and include, but are not limited to, disulfide linkers (1), acid labile linkers (2, 3, 4 and 5; including dialkoxybenzyl linkers (e.g., 2), Sieber linkers (e.g., 3), indole linkers (e.g., 4), t-butyl Sieber linkers (e.g., 5)), electrophilically cleavable linkers, nucleophilically cleavable linkers, photocleavable linkers, cleavage under reductive conditions, oxidative conditions, cleavage via use of safety-catch linkers, and cleavage by elimination mechanisms.

A. Electrophilically Cleaved Linkers.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system (e.g., as is shown in FIG. 3 as O—C($R_4$)($R_5$)—O—$R_6$.

The use of thiophilic metals, such as nickel, silver or mercury, in the cleavage of thioacetal or other sulphur-containing protecting groups can also be considered for the preparation of suitable linker molecules.

B. Nucleophilically Cleaved Linkers.

Nucleophilic cleavage is also a well recognised method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers.

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenyl compounds and nitroveratryl compounds. Linkers based on benzoin chemistry can also be used (Lee et al., *J. Org. Chem.* 64:3454–3460, 1999).

D. Cleavage Under Reductive Conditions

There are many linkers known that are susceptible to reductive cleavage. Catalytic hydrogenation using palladium-based catalysts has been used to cleave benzyl and benzyloxycarbonyl groups. Disulphide bond reduction is also known in the art.

E. Cleavage Under Oxidative Conditions

Oxidation-based approaches are well known in the art. These include oxidation of p-alkoxybenzyl groups and the oxidation of sulphur and selenium linkers. The use of aqueous iodine to cleave disulphides and other sulphur or selenium-based linkers is also within the scope of the invention.

F. Safety-catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., *J. Org. Chem.* 62:5165–5168, 1997).

G. Cleavage by Elimination Mechanisms

Elimination reactions can also be used. For example, the base-catalysed elimination of groups such as Fmoc and cyanoethyl, and palladium-catalysed reductive elimination of allylic systems, can be used.

As well as the cleavage site, the linker can comprise a spacer unit. The spacer distances the nucleotide base from the cleavage site or label. The length of the linker is unimportant provided that the label is held a sufficient distance from the nucleotide so as not to interfere with any interaction between the nucleotide and an enzyme.

The modified nucleotides can also comprise additional groups or modifications to the sugar group. For example, a dideoxyribose derivative, lacking two oxygens on the ribose ring structure (at the 2' and 3' positions), can be prepared and used as a block to further nucleotide incorporation on a growing oligonucleotide strand. The ribose ring can also be modified to include a protecting group at the 3' position or a group that can be transformed or modified to form a 3' OH group. The protecting group is intended to prevent nucleotide incorporation onto a nascent polynucleotide strand, and can be removed under defined conditions to allow polymerisation to occur. In contrast to the prior art, there is no detectable label attached at the ribose 3' position. This ensures that steric hindrance with the polymerase enzyme is reduced, while still allowing control of incorporation using the protecting group.

The skilled person will appreciate how to attach a suitable protecting group to the ribose ring to block interactions with the 3'-OH. The protecting group can be attached directly at the 3' position, or can be attached at the 2' position (the protecting group being of sufficient size or charge to block interactions at the 3' position). Alternatively, the protecting group can be attached at both the 3' and 2' positions, and can be cleaved to expose the 3'OH group.

Suitable protecting groups will be apparent to the skilled person, and can be formed from any suitable protecting group disclosed in Green and Wuts, supra. Some examples of such protecting groups are shown in FIG. 3. The protecting group should be removable (or modifiable) to produce a 3' OH group. The process used to obtain the 3' OH group can be any suitable chemical or enzymic reaction.

The labile linker may consist of functionality cleavable under identical conditions to the block. This will make the deprotection process more efficient as only a single treatment will be required to cleave both the label and the block. Thus the linker may contain functional groups as described in FIG. 3, which could be cleaved with the hydroxyl functionality on either the residual nucleoside or the removed label. The linker may also consist of entirely different chemical functionality that happens to be labile to the conditions used to cleave the block.

The term "alkyl" covers both straight chain and branched chain alkyl groups. Unless the context indicates otherwise, the term "alkyl" refers to groups having 1 to 8 carbon atoms, and typically from 1 to 6 carbon atoms, for example from 1 to 4 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of cycloalkyl groups are those having from 3 to 10 ring atoms, particular examples including those derived from cyclopropane, cyclobutane, cyclopentane, cyclohexane and cycloheptane, bicycloheptane and decalin.

Examples of alkenyl groups include, but are not limited to, ethenyl (vinyl), 1-propenyl, 2-propenyl (allyl), isopropenyl, butenyl, buta-1,4-dienyl, pentenyl, and hexenyl.

Examples of cycloalkenyl groups include, but are not limited to, cyclopropenyl, cyclobutenyl, cyclopentenyl, cyclopentadienyl and cyclohexenyl.

The term alkoxy refers to $C_{1-6}$ alkoxy unless otherwise indicated: —OR, wherein R is a $C_{1-6}$ alkyl group. Examples of $C_{1-6}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBU) (sec-butoxy), —O(iBu) (isobutoxy), and —O(tBu) (tert-butoxy).

The term amino refers to groups of type $NR^1R^2$, wherein $R^1$ and $R^2$ are independently selected from hydrogen, a $C_{1-6}$ alkyl group (also referred to as $C_{1-6}$ alkylamino or di-$C_{1-6}$ alkylamino).

The term "halogen" as used herein includes fluorine, chlorine, bromine and iodine.

The nucleotide molecules of the present invention are suitable for use in many different methods where the detection of nucleotides is required.

DNA sequencing methods, such as those outlined in U.S. Pat. No. 5,302,509 can be carried out using the nucleotides.

A method for determining the sequence of a target polynucleotide can be carried out by contacting the target polynucleotide separately with the different nucleotides to form the complement to that of the target polynucleotide, and detecting the incorporation of the nucleotides. Such a method makes use of polymerisation, whereby a polymerase enzyme extends the complementary strand by incorporating the correct nucleotide complementary to that on the target. The polymerisation reaction also requires a specific primer to initiate polymerisation.

For each cycle, the incorporation of the labelled nucleotide is carried out by the polymerase enzyme, and the incorporation event is then determined. Many different polymerase enzymes exist, and it will be evident to the person of ordinary skill which is most appropriate to use. Preferred enzymes include DNA polymerase I, the Klenow fragment, DNA polymerase III, T4 or T7 DNA polymerase, Taq polymerase or vent polymerase. A polymerase engineered to have specific properties can also be used.

The sequencing methods are preferably carried out with the target polynucleotide arrayed on a solid support. Multiple target polynucleotides can be immobilised on the solid support through linker molecules, or can be attached to particles, e.g., microspheres, which can also be attached to a solid support material.

The polynucleotides can be attached to the solid support by a number of means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides and beads, ceramic and silicon surfaces and plastic materials. The support is usually a flat surface although microscopic beads (microspheres) can also be used and can in turn be attached to another solid support by known means. The microspheres can be of any suitable size, typically in the range of from 10 nm to 100 nm in diameter. In a preferred embodiment, the polynucleotides are attached directly onto a planar surface, preferably a planar glass surface. Attachment will preferably be by means of a covalent linkage. Preferably, the arrays that are used are single molecule arrays that comprise polynucleotides in distinct optically resolvable areas, e.g., as disclosed in International App. No. WO 00/06770.

The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed.

The method makes use of the polymerisation reaction to generate the complementary sequence of the target. The conditions necessary for polymerisation to occur will be apparent to the skilled person.

To carry out the polymerase reaction it will usually be necessary to first anneal a primer sequence to the target polynucleotide, the primer sequence being recognised by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e., a hairpin loop structure. This structure may be immobilised to the solid support at any point on the molecule. Other conditions necessary for carrying out the polymerase reaction, including temperature, pH, buffer compositions etc., will be apparent to those skilled in the art.

The modified nucleotides of the invention are then brought into contact with the target polynucleotide, to allow polymerisation to occur. The nucleotides may be added sequentially, i.e., separate addition of each nucleotide type (A, T, G or C), or added together. If they are added together, it is preferable for each nucleotide type to be labelled with a different label.

This polymerisation step is allowed to proceed for a time sufficient to allow incorporation of a nucleotide.

Nucleotides that are not incorporated are then removed, for example, by subjecting the array to a washing step, and detection of the incorporated labels may then be carried out.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualise the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g., 10 nm to 10 µm. For a description of scanning near-field optical microscopy, see Moyer et al., *Laser Focus World* 29:10, 1993. Suitable apparatus used for imaging polynucleotide arrays are known and the technical set-up will be apparent to the skilled person.

After detection, the label may be removed using suitable conditions that cleave the linker.

The use of the modified nucleotides is not limited to DNA sequencing techniques, and other techniques, including polynucleotide synthesis, DNA hybridisation assays and single nucleotide polymorphism studies, may also be carried out using nucleotides of the invention. Any technique that involves the interaction between a nucleotide and an enzyme may make use of the molecules of the invention. For example, the molecule may be used as a substrate for a reverse transcriptase or terminal transferase enzyme.

Suitable structures are described in the following Examples and are shown in the accompanying drawings.

EXAMPLES
Example 1
Synthesis of Disulfide Linker 5
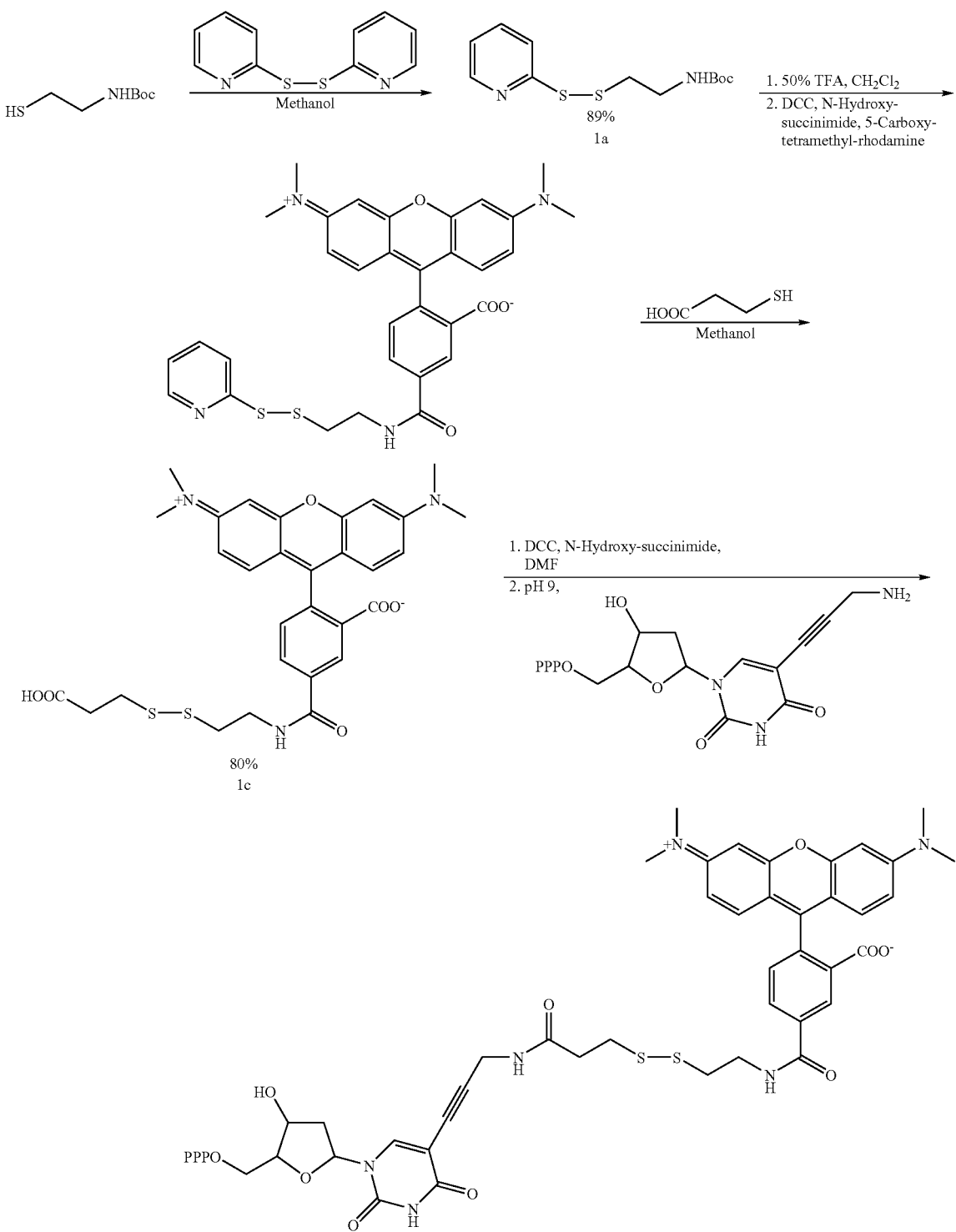

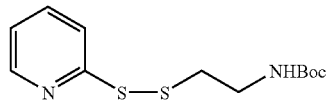

1a tButyl-N-(2-mercaptoethyl) carbamate (3 mmol, 0.5 mL) was added dropwise to a solution of 1.32 g (6.0 mmol) aldrithiol in 15 mL MeOH. After 1.5 h the reaction had gone to completion and the solvent was evaporated. The crude product was purified by chromatography on silica with ethyl acetate:petroleum ether (1:4). Product 1a was obtained as a slightly yellow oil (0.76 g, 2.67 mmol, 89%). $^1$H NMR (500 Mhz, $D_6$-DMSO): δ=1.38 (s, 9 H, tBu), 2.88 (t, J=6.6 Hz, 2 H, $SCH_2$)3.20(q, J=6.6 Hz, 2 H, $CH_2$NH), 7.02 (bs, 1 H, NH), 7.24 (ddd, J=7.3 Hz, J=4.9 Hz, J=1.0 Hz, 1 H, H-5), 7.77 (dt, J=8.1 Hz, J=1.0 Hz, 1 H, H-3), 7.82 (ddd, J=8.1 Hz, J=7.4 Hz, J=1.8 Hz, 1 H, H-4), 8.46 (ddd, J=4.9 Hz, J=1.8 Hz, J=1.0 Hz, 1 H, H-6).

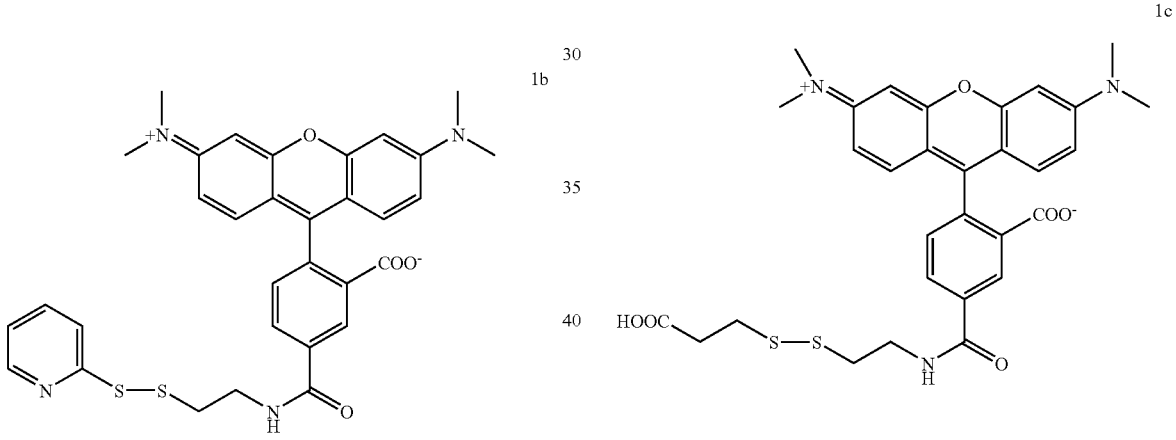

1b

1c

To deprotect the amine of 1a, 17 mg of 1a (60 μmol) was dissolved in a mixture of 0.5 mL DCM and 0.5 mL trifluoracetic acid. This mixture was stirred for 2.5 h at rt and then the solvents were removed under reduced pressure. The residue was three times redissolved in 2 mL DCM and evaporated to dryness. The deprotected product was dried under high vacuum for 3 h and then dissolved in 1 mL dry DMF. It was assumed that the deprotection had gone to completion.

To a solution of 15 mg 5-carboxy tetra methyl rhodamine (35 μmol) in 2 mL DMF were added 8.0 mg N-hydroxy succinimide (70 μmol) and 7.8 mg DCC (38 μmol). The mixture was stirred for 6 h in the dark. Then 22 μl DIPEA (126 μmol) and the solution of deprotected 1a in 1 mL DMF were added. After stirring the reaction mixture overnight in the dark, the solvent was removed under reduced pressure. The residue was dissolved in DCM and washed with saturated NaCl solution. After drying over $MgSO_4$ the crude mixture was purified on silica with $CHCl_3$:MeOH (3:1) as solvent. 1b was isolated as a dark red solid in 90% yield (19.2 mg, 31.4 μmol). $^1$H NMR (500 MHz, $D_6$-DMSO): δ=3.09 (t, J=6.7 Hz, 2 H, $SCH_2$), 3.63 (q, J=6.2 Hz, 2 H, $CH_2$NH), 6.48–6.53 (m, 6 H, H-Anthracene), 7.23–7.26 [m, 1 H, H-5 (pyridine)], 7.32 ( d, J=7.9 Hz, 1 Hz, H-3), 7.81–7.82 [m, 2 H, H-3+H-4 (pyridine)], 8.21 (d, J=7.9 Hz, 1 H, H-4), 8.43 (s, 1 H, H-6), 8.47 [dt, J=4.7 Hz, J=1.3 Hz, 1 H, H-6 (pyridine)], 9.03 (t, J=5.2 Hz, 1 H, NH).

Mercaptopropionic acid (20.6 μmol, 1.8 μl) was added to a solution of 19.6 mg 1b (32.7 μmol) in 2 mL MeOH. The mixture was stirred for 2.5 h in the dark. The solvent was removed under reduced pressure. The crude product was purified by chromatography on silica with $CHCl_3$:MeOH: AcOH 15:1:0.5 as the solvent mixture. 15.5 mg (26 μmol, 80%) dark red crystals 1c could be isolated. $^1$H NMR (500 MHz, $D_2O$): δ=2.53 (t, J=7.0 Hz, 2 H, $CH_2$COOH), 2.88 (t, J=7.0 Hz, 2 H, $CH_2CH_2$COOH), 2.96–2.99 (m, 2 H, $CH_2CH_2$NH), 3.73 (t, J=6.3 Hz, 2 H, $CH_2$NH), 6.53 (d, J=2.4 Hz, 2 H, H-Anthracene), 6.81 (dd, J=9.5 Hz, J=4.5 Hz, 2 H, H-Anthracene), 7.12 (d, J=9.5 Hz, 2 H, H-Anthracene), 7.48 (d, J=7.9 Hz, 1 H, H-3), 7.95 (dd, J=8.1 Hz, J=1.9 Hz, 1 H, H-2) 8.13 (d, J=1.9 Hz, 1 H, H-1). +ve electro spray ($C_{30}H_{31}N_3O_6S_2$): expected 593.17; found 594.3 [M+H], 616.2 [M+Na].

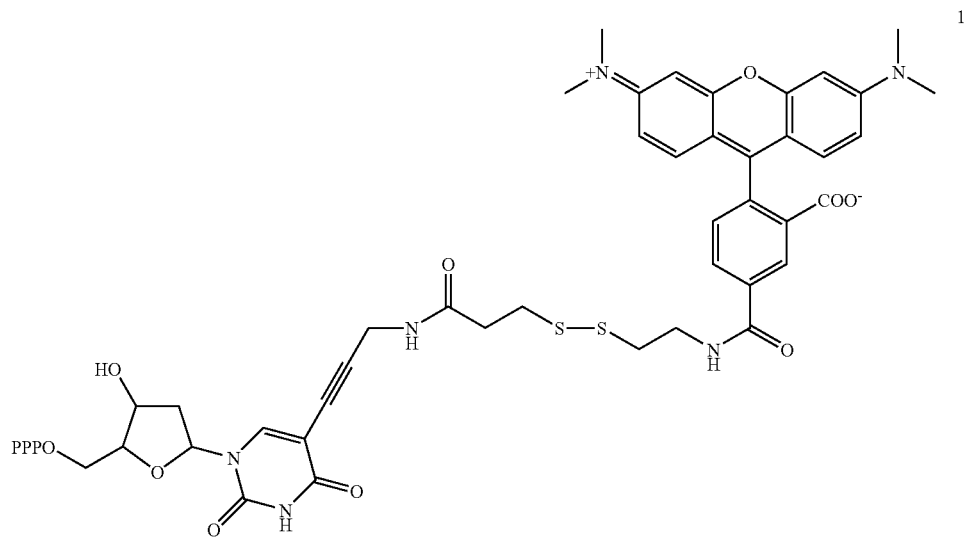

To a solution of 25.8 mg 1c (43.4 μmol) in 3 mL DMF (dry) were added 9.9 mg N-hydroxy succinimide (86.8 μmol) and 9.7 mg DCC (47.1 μmol). The mixture was stirred in the dark for 5 h at room temperature and then put in the fridge overnight. The mixture was filtered through a plug of cotton wool in a new flask and to this was added a solution of 865 μl propargylamino dUTP (14.7 μmol, 17 μmol in 1 mL H$_2$O) and 3 mL sodium borate buffer (0.1 M solution, pH 9). The mixture was stirred overnight. After removal of solvents the residue was dissolved in as little water as possible and purified by HPLC. A Zorbax C18 column was used with 0.1 M triethyl ammonium bicarbonate (TEAB) and acetonitrile as buffers. $^{31}$P NMR (400 MHz, D$_2$O): δ=−4.73 (d), −9.93 (d), 19.03 (t). −ve electro spray (C$_{42}$H$_{47}$N$_6$O$_{19}$P$_3$S$_2$ assuming 4 H$^+$ counter ions): expected 1096.16; found 1092.9. UV in Water: λ$_{(max)}$=555 nm A$_{(555)}$=0.885 (c=0.036 μmol).

Triphosphate (1) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 μM compound 3, 100 nM DNA template (previously labelled with P32 and T4 polynucleotide kinase) and 10 units of commercial exo-Klenow (Amersham Corp., Arlington Heights, Ill., USA). The DNA templates were self-complementary hairpins (5'-TACCgTCgACgTCgACgCTggCg-AgCgTgCTgCggTTTTT(C6-amino)TTACCgCAg-CACgCTCgCCAgCg; SEQ ID NO:1). The reaction was performed in 100 μL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (disulfide linker gel, FIG. 3). A second set of lanes is shown in which the material is exposed to DTT after the incorporation. A different band shift can be seen which shows removal of the dye from the DNA construct, thus a cycle of polymerase incorporation and cleavage has been shown using this disulfide compound.

Example 2

Synthesis of TMR-Sieber Linker Free Acid

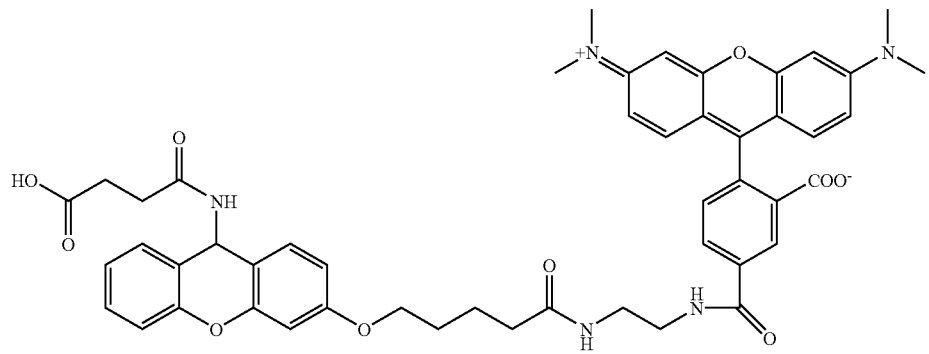

5-[-9-[9-(fluorenyl-methyloxycarbonyl)amino]xanthen-3-yl]valeric acid, (42.8 mg, 80 μmol) was stirred at room temperature with disuccinimidyl carbonate (22.5 mg, 88 μmol) and N,N-dimethyl aminopyridine (10.8 mg, 88 μmol) in DMF. After 5 minutes, mono-5-carboxy TMR ethylene diamine (198.9 mg, 40 μmol) was added followed by DIPEA (13.9 μl, 80 μmol). The reaction was stirred at room temperature. After 2 hrs, the reaction mixture was diluted with dichloromethane (100 mL) and the resulting solution was extracted with 1 M aqueous potassium dihydrogen phosphate (50 mL). The DCM layer was separated and evaporated under reduced pressure. The residue was purified by a short column chromatography. The fractions eluting with 40% methanol in chloroform were collected and evaporated under reduced pressure. The residue was then dissolved in dry DMF (1 mL) and N-(2-mercaptoethyl)aminomethyl polystyrene (200 mg, 400 μmol) and DBU (12 μl, 80 μmol). After 10 minutes at room temperature, the resins were filtered off and rinsed with dry DMF (1 mL). All the filtrates were combined and then added to a solution of succinic anhydride (80 mg, 800 μmol), DIPEA (139 μl, 800 μmol) and DMAP (9.8 mg, 80 μmol) in DMF (1 mL). The reaction mixture was then stirred at room temperature. After overnight (16 hrs), all the solvents were evaporated under reduced pressure and the residue was purified by a short column chromatography. The title compound eluted with 30% methanol in chloroform was obtained as purple powders (22 mg, overall yield 63%). $^1$HNMR [D$_6$-DMSO]: 8.82 (1H, t, J 5.4, ex.), 8.75 (1H, d, J 8.9, ex.), 8.42 (1H, d, J 1.5), 8.20 (1H, dd, J 8.0 and 1.5), 7.95 (1H, t, J 5.9, ex.), 7.34 (1H, d, J 7.3), 7.30–7.27 (2H, m), 7.21 (1H, d, J 8.5), 7.16–7.07 (2H, m), 6.68 (1H, dd, J 8.8 and 2.5), 6.65 (1H, d, J 2.4), 6.49–6.43 (6H, m), 6.18 (1H, d, J 5.6), 3.95 (1H, t, J 5.9), 3.39–3.36 (2H, m), 3.30–3.27 (2H, m), 2.92 (12H, s), 2.37–2.33 (2H, m), 2.14(2H, t, J 7.2) and 1.70–1.62 (4H, m). MS[(ES(+)], m/z 868.5 (MH$^+$).

Example 3

Synthesis of TMR-Sieber Linker-dUTP (3)

TMR-sieber linker free acid (4.34 mg, 5 μmol) was stirred with disuccinimidyl carbonate (1.74 mg, 7.5 μmol) and N,N-dimethyl aminopyridine (0.92 mg, 7.5 μmol) in DMF (1 mL) at room temperature. After 10 minutes, all the reaction mixture was added to tetra-(tri-butylammonium) salt of 5-(3-aminopropynyl)-2'-deoxyuridine-5'-triphosphate (10 μmol). The reaction was stirred at room temperature for 4 hrs and stored in the fridge overnight. The reaction mixture was then diluted with chilled water (10 mL) and all the resulting solution was applied onto a short column of DEAE A-25. The column was initially eluted with 0.1 M TEAB buffer and then 0.7 M TEAB buffer. The 0.7 M TEAB eluents were collected and evaporated under reduced pressure. The residue was co-evaporated with MeOH (2×10 mL) and then purified by preparative HPLC. The title compound was obtained as triethylammonium salt in 31% yield (based on the quantification of TMR at 555 nm in water (pH 7)). $^1$HNMR in D$_2$O indicated two diastereoisomers, due to the sieber linker moiety and there were approximately three triethylammonium count ions. $^1$HNMR [D$_2$O]: 8.18 (1H, m), 8.06 (1H, m), 7.76 (0.55H, s), 7.74 (0.45H, s), 7.36–7.09 (5H, m), 6.89–6.72 (3H, m), 6.59–6.37 (5H, m), 6.12 (0.55H, t, J 6.6), 6.05 (0.45H, t, J 6.6), 5.99 (0.45H, d, J 2.5), 5.91 (1.1H, m), 5.88 (0.45H, s), 4.49 (0.55H, m), 4.43 (0.45H, m), 4.00–3.35 (9H, m), 3.30–2.95 (32H, m), 2.65–2.52 (4H, m), 2.25–2.05 (4H, m), 1.62–1.42 (4H, m) and 1.23 (27H, t, J 7.3). $^{31}$P [D$_2$O]: −9.91 ($^\gamma$P, d, J 19.2), [−11.08($^\alpha$P, d, J 20.1) and −11.30 ($^\alpha$P, d, J 20.1), due to two diastereoisomers] and −22.57 ($^\beta$P, m). MS[(ES(−)], m/z 1369.1 (M$^-$).

Triphosphate (3) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 μM compound 3, 100 nM DNA template (previously labelled with P32 and T4 polynucleotide kinase) and 10 units of commercial exo-Klenow (Amersham Corp. Arlington Heights, Ill., USA). The DNA templates were self-complementary hairpins (5'-TACCgTCgACgTCgACgCTggCg-AgCgTgCTgCggTTTTT(C6-amino)TTACCgCAg-CACgCTCgCCAgCg; SEQ ID NO:1). The reaction was performed in 100 μL volume at 37° C. with timepoints taken at 0, 1, 3, 5 and 10 min. The reaction products were electrophoresed down a denaturing (8 M urea) 20% polyacrylamide gel and imaged on a typhoon phosphorimager.

Figure 4:
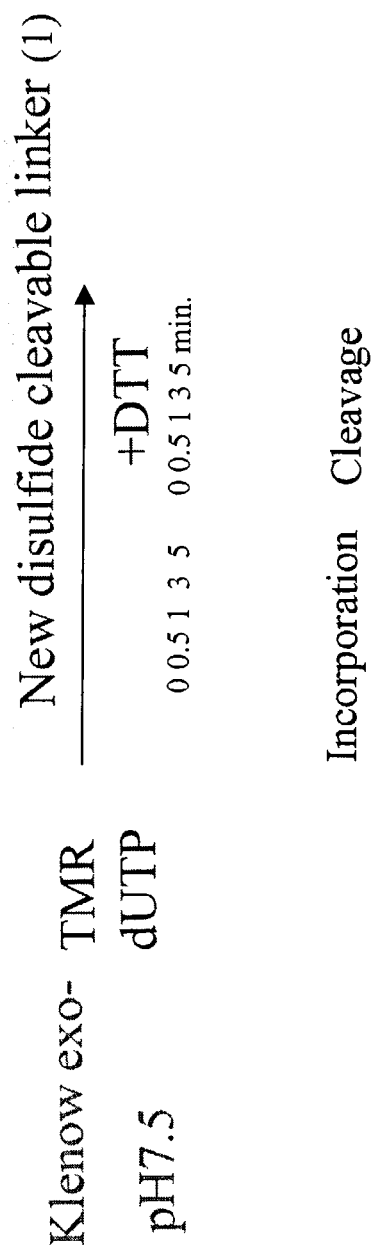
FIG. 4 shows a denaturing gel showing the incorporation of the triphosphate of Example 1 using Klenow polymerase.

Complete single base extension was seen in 1 minute indicating efficient polymerase incorporation (Sieber linker gel, FIG. 4).

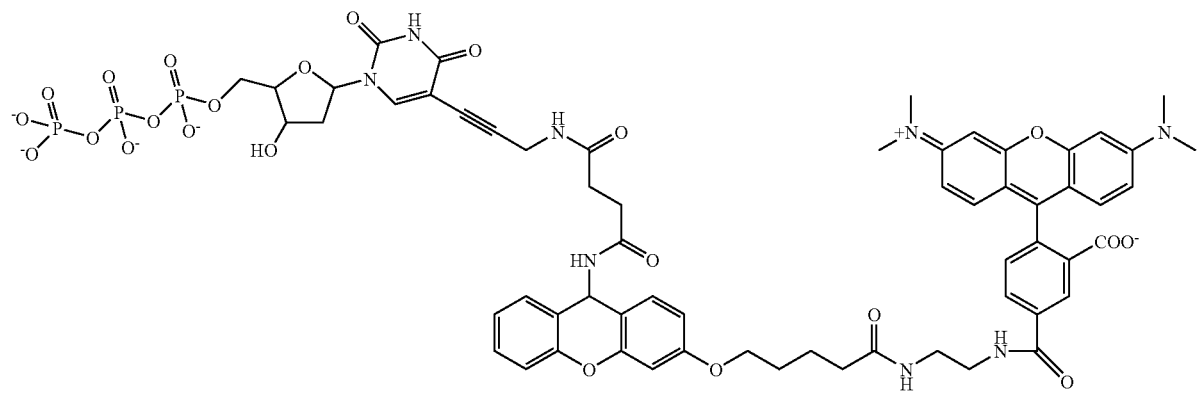

Example 4

Synthesis of TMR-Indole Linker-dUTP (4)

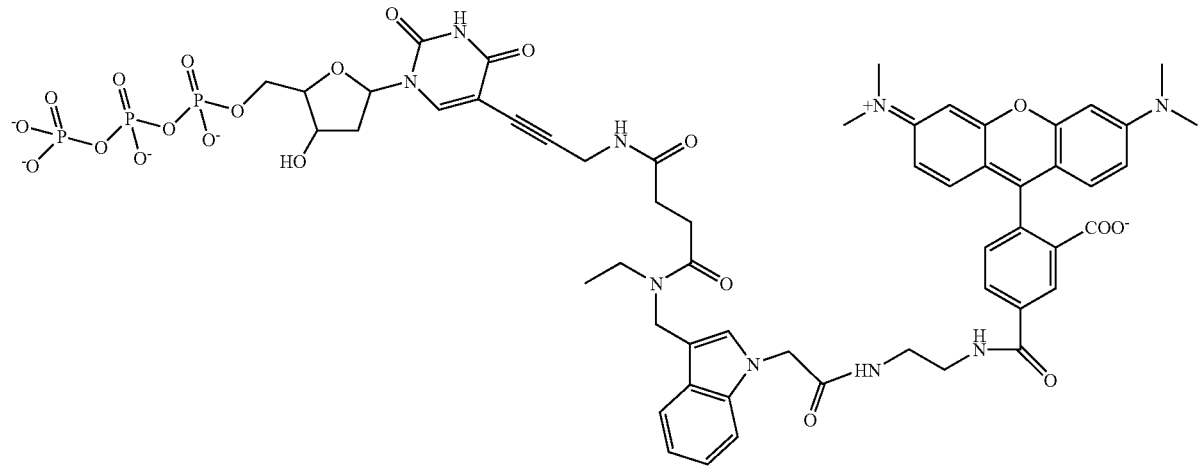

Figure 5:
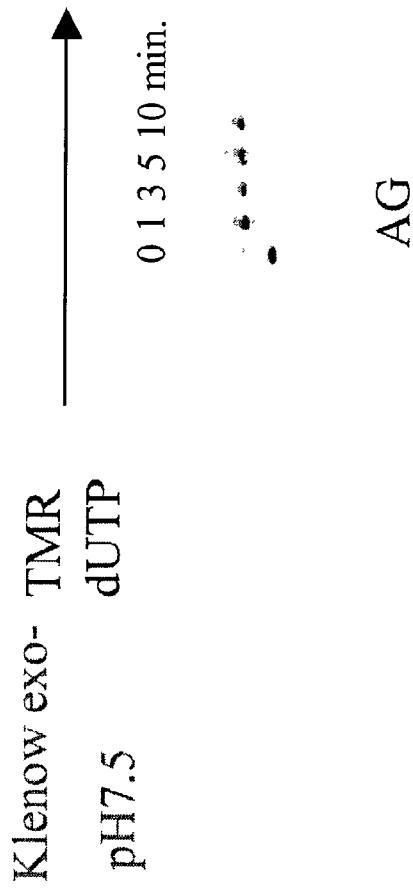
FIG. 5 shows a denaturing gel showing the incorporation of the triphosphate of Example 3 using Klenow polymerase.
Figure 6:
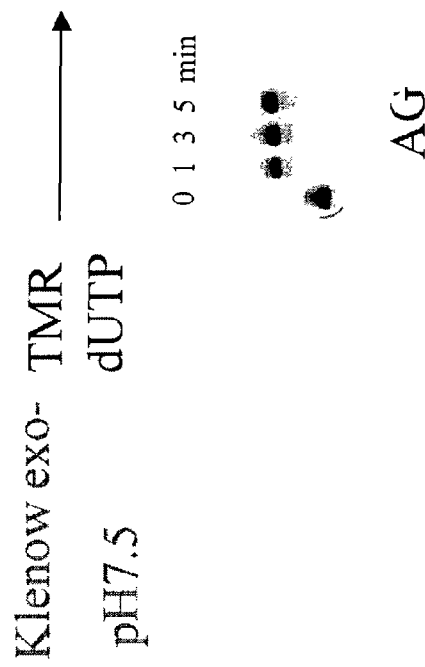
FIG. 6 shows a denaturing gel showing the incorporation of the triphosphate of Example 4 using Klenow polymerase.

Triphosphate (4) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp., Arlington Heights, Ill., USA). The DNA templates were self-complementary hairpins (5'-TACCgTCgACgTCgACgCTggCg-AgCgTgCTgCggTTTTT(C6-amino)TTACCgCAg-CACgCTCgCCAgCg; SEQ ID NO:1). The reaction was performed in 100 µL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (indole linker gel, FIG. 5).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A nucleotide or nucleoside molecule, having a base that is linked to a detectable label via a cleavable linker, wherein the molecule has a ribose or deoxyribose sugar moiety comprising a protecting group attached via the 2' or 3' oxygen atom and the cleavable linker and the protecting group are cleavable under identical conditions.

2. The molecule of claim 1, wherein the base is a purine, or a pyrimidine.

3. The molecule of claim 2, wherein the base is a deazapurine.

4. The molecule of claim 1, that is a deoxyribonucleotide triphosphate.

5. The molecule of claim 1, wherein the detectable label is a fluorophore.

6. The molecule of claim 1, wherein the linker is acid labile, photolabile or contains a disulphide linkage.

7. A kit, comprising:
(a) individual nucleotides, wherein each nucleotide has a base that is linked to a detectable label via a cleavable linker, and wherein the detectable label linked to each nucleotide can be distinguished upon detection from the detectable label used for other three nucleotides, and each of said individual nucleotides has a deoxyribose sugar moiety comprising a protecting group attached via the 2' or 3' oxygen atom and the cleavable linker and the protecting group are cleavable under identical conditions; and
(b) packaging materials therefor.

8. The kit of claim 7, further comprising an enzyme and buffers appropriate for the action of the enzyme.

* * * * *